United States Patent
Roeder et al.

(10) Patent No.: US 11,033,294 B2
(45) Date of Patent: Jun. 15, 2021

(54) METHOD OF TREATMENT FOR AORTIC DISSECTION

(71) Applicant: COOK MEDICAL TECHNOLOGIES LLC, Bloomington, IN (US)

(72) Inventors: Blayne A. Roeder, Bloomington, IN (US); Joshua F. Krieger, Topsfield, MA (US); Jarin A. Kratzberg, West Lafayette, IN (US); Matthew J. Phillips, Carlsbad, CA (US); Zachary Berwick, Costa Mesa, CA (US); Ghassan Kassab, La Jolla, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 187 days.

(21) Appl. No.: 15/896,814

(22) Filed: Feb. 14, 2018

(65) Prior Publication Data
US 2018/0256189 A1    Sep. 13, 2018

Related U.S. Application Data

(60) Provisional application No. 62/470,680, filed on Mar. 13, 2017.

(51) Int. Cl.
*A61B 17/3205* (2006.01)
*A61F 2/86* (2013.01)
(Continued)

(52) U.S. Cl.
CPC .. *A61B 17/3205* (2013.01); *A61B 17/320016* (2013.01); *A61B 18/1492* (2013.01);
(Continued)

(58) Field of Classification Search
CPC .... A61F 2/07; A61F 2/95; A61F 2/954; A61F 2002/9505
See application file for complete search history.

(56) References Cited

U.S. PATENT DOCUMENTS 4,043,342 A    8/1977   Morrison, Jr.
4,791,843 A   12/1988   Herrington et al.
(Continued)

FOREIGN PATENT DOCUMENTS

DE    102012203783 A1    3/2013
WO    WO 97/12555        4/1997
(Continued)

OTHER PUBLICATIONS

European Search Report for corresponding European Application No. 18275021, dated Aug. 8, 2018, 8 pages.
(Continued)

*Primary Examiner* — Todd J Scherbel
(74) *Attorney, Agent, or Firm* — Brinks Gilson & Lione

(57) ABSTRACT

A method of treatment for a body vessel is provided. The body vessel includes a dissection flap formed from a wall of the body vessel, which longitudinally separates a natural body vessel lumen into a true lumen and a false lumen. One or more cuts are formed in the dissection flap with a cutting device or system. An expandable device is inserted within the true lumen, and expanded to reappose the dissection flap against the wall of the body vessel where the dissection flap was detached from the wall such that the false lumen is closed. A variety of cut patterns are disclosed.

20 Claims, 8 Drawing Sheets

(51) Int. Cl.
*A61B 17/32* (2006.01)
*A61B 18/14* (2006.01)
*A61F 2/07* (2013.01)
*A61B 17/12* (2006.01)
*A61B 17/22* (2006.01)
*A61F 2/82* (2013.01)
*A61B 17/00* (2006.01)
*A61F 2/90* (2013.01)
*A61B 18/00* (2006.01)

(52) U.S. Cl.
CPC .......... *A61F 2/86* (2013.01); *A61B 17/12109* (2013.01); *A61B 17/32053* (2013.01); *A61B 18/1402* (2013.01); *A61B 2017/00292* (2013.01); *A61B 2017/00778* (2013.01); *A61B 2017/00876* (2013.01); *A61B 2017/22038* (2013.01); *A61B 2018/00404* (2013.01); *A61B 2018/00416* (2013.01); *A61B 2018/00601* (2013.01); *A61F 2/07* (2013.01); *A61F 2/90* (2013.01); *A61F 2002/823* (2013.01)

(56) References Cited

U.S. PATENT DOCUMENTS

| | | |
|---|---|---|
| 5,449,355 A | 9/1995 | Rhum et al. |
| 5,683,384 A | 11/1997 | Gough et al. |
| 5,702,412 A | 12/1997 | Popov et al. |
| 6,001,093 A | 12/1999 | Swanson et al. |
| 6,068,637 A | 5/2000 | Popov et al. |
| 6,068,638 A | 5/2000 | Makower |
| 6,238,392 B1 | 5/2001 | Long |
| 7,387,636 B2 | 6/2008 | Cohn et al. |
| 8,021,359 B2 | 9/2011 | Auth et al. |
| 8,142,427 B2 | 3/2012 | Pearson |
| 8,491,613 B2 | 7/2013 | Bliss et al. |
| 8,696,662 B2 | 4/2014 | Eder et al. |
| 8,845,635 B2 | 9/2014 | Daniel et al. |
| 8,977,333 B2 | 3/2015 | Anderson |
| 9,017,323 B2 | 4/2015 | Miller et al. |
| 9,023,031 B2 | 5/2015 | Ingle et al. |
| 9,168,082 B2 | 10/2015 | Evans et al. |
| 9,393,100 B2 | 7/2016 | Schreck |
| 9,681,915 B2 | 6/2017 | Berguer et al. |
| 2004/0082850 A1 | 4/2004 | Bonner et al. |
| 2004/0176832 A1 | 9/2004 | Hartley et al. |
| 2005/0187545 A1 | 8/2005 | Hooven et al. |
| 2006/0142836 A1 | 6/2006 | Hartley et al. |
| 2008/0065019 A1 | 3/2008 | Heuser et al. |
| 2008/0091264 A1 | 4/2008 | Machold et al. |
| 2008/0108904 A1 | 5/2008 | Heil |
| 2008/0312646 A9 | 12/2008 | Auth et al. |
| 2009/0093802 A1 | 4/2009 | Kulesa et al. |
| 2009/0099650 A1* | 4/2009 | Bolduc ............... A61F 2/07 623/1.36 |
| 2009/0299402 A1 | 12/2009 | Orihashi et al. |
| 2011/0144672 A1 | 6/2011 | Bliss et al. |
| 2011/0288544 A1 | 11/2011 | Verin et al. |
| 2012/0130363 A1 | 5/2012 | Kim et al. |
| 2012/0302935 A1 | 11/2012 | Miller et al. |
| 2013/0172877 A1 | 7/2013 | Subramaniam |
| 2013/0231658 A1 | 9/2013 | Wang |
| 2013/0253632 A1 | 9/2013 | Schreck |
| 2014/0107642 A1 | 4/2014 | Rios et al. |
| 2015/0080886 A1 | 3/2015 | Miller et al. |
| 2015/0306282 A1 | 10/2015 | Scanlon |
| 2015/0313668 A1 | 11/2015 | Miller et al. |
| 2016/0228181 A1 | 8/2016 | Berguer et al. |
| 2018/0256190 A1* | 9/2018 | Roeder ............. A61B 17/3205 |

FOREIGN PATENT DOCUMENTS

| | | |
|---|---|---|
| WO | WO 2008/081613 A1 | 7/2008 |
| WO | WO 2012/068273 A1 | 5/2012 |
| WO | WO 2015/108984 A1 | 7/2015 |

OTHER PUBLICATIONS

Communication for EP Application No. 18275021.6 dated Jul. 4, 2019, 5 pages.
Extended European Search Report in European Application No. 18275022.4 dated Jun. 21, 2018, 8 pages.
R. Berguer, et al., Experimental and Clinical Evidence Supporting Septectomy in the Primary Treatment of Acute Type B Thoracic Aortic Dissection, *Ann Vasc Surg.*, Feb. 2015, vol. 29, No. 2, pp. 167-173.
Extended European Search Report for EP Application No. 20199937.2 dated Jan. 29, 2021, 7 pages.

\* cited by examiner

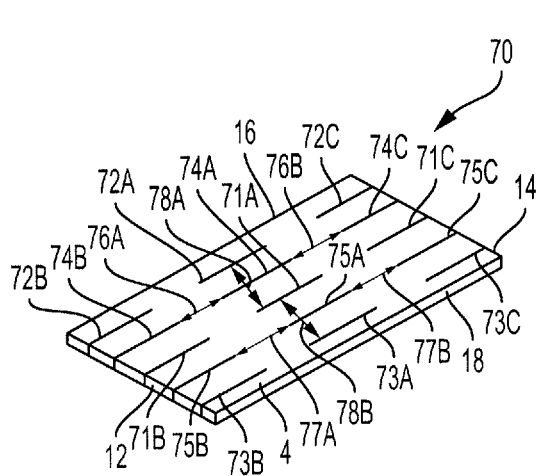

METHOD OF TREATMENT FOR AORTIC DISSECTION

CROSS-REFERENCE TO RELATED APPLICATIONS

This application claims priority and the benefit of U.S. provisional Patent Application Ser. No. 62/470,680, filed Mar. 13, 2017, which is incorporated herein by reference in its entirety.

BACKGROUND

The present disclosure relates generally to medical method of treatments, and particularly, to techniques and patterns for cutting tissue walls for medical treatment, such as, for example, for treatment of aortic dissection.

An aortic dissection is a form of aneurysm to the descending aorta (referred to as Type B dissections) in which the wall of the aorta is damaged to such an extent that blood under pressure can get between inner and outer layers of the wall of the aorta to expand part of the wall into an inflated sac of blood which is referred to as a false lumen. The inflated sac of blood or false lumen so formed may extend some distance down the descending aorta and open out into the aorta again further down. In the acute phase, dissections may close off perfusion from the aorta to vital organs. In the chronic phase, the weakened tissue can develop into aneurysm and ultimately rupture. Dissections involving the ascending aorta are referred to as Type A dissections.

Patients with acute aortic dissection (that is less than two weeks from onset) presenting with or without complicating factors such as malperfusion syndrome and impending aortic rupture represent a high risk cohort even with intervention and/or medical management. Endovascular aortic repair (EVAR) is one approach for acute, complicated aortic dissections. This approach involves stenting the aorta at the level of the primary entry tear (and to varying extents distally) to restore the true lumen flow and eliminate flow through the false lumen by complete reapposition of the dissection flap to the aortic wall. Restoration of the true lumen by this approach has been found to improve outcomes based on false lumen thrombosis and aortic remodeling. However, due to dynamic changes to the dissection flap (for example, contraction, remodeling, etc.) it is often difficult to completely reappose the flap with current techniques. For instance, it has been observed in some patients under EVAR treatment, the continued false lumen patency contributes to aneurysmal formation. There is a need for an improved method to treat aortic dissections. The current application provides novel solutions to the treatment of aortic dissections.

SUMMARY

Methods of treatment of a body vessel, such as an aortic dissection, are disclosed. In one example, a method of treatment for a body vessel. The body vessel includes a dissection flap formed from a wall of the body vessel. The dissection flap is longitudinally separating a natural body vessel lumen into a true lumen and a false lumen. The method includes one or more of the following steps. A step includes positioning a cutting device within at least one of a true lumen and a false lumen and along a dissection flap. A step includes forming a cut in the dissection flap with the cutting device. A step includes positioning an expandable device within the true lumen along the cut formed in the dissection flap. A step includes radially expanding the expandable device to reappose the dissection flap with the cut against the wall of the body vessel where the dissection flap was detached from the wall such that the false lumen is closed off.

In another example, a method includes a step of forming a cut pattern in a dissection flap with a cutting system. The cut pattern includes a first cut and a second cut circumferentially spaced and longitudinally offset from another. A step includes positioning an expandable device within the true lumen and along the cut pattern formed in the dissection flap. A step includes expanding the expandable device to reappose the dissection flap with the cut pattern against the wall of the body vessel where the dissection flap was detached from the wall such that the false lumen is closed.

In another example, a method includes a step of forming a cut pattern in a dissection flap. The cut pattern includes a first row of first cuts and a second row of second cuts circumferentially spaced from the first row. The first cuts are longitudinally spaced from another and the second cuts are longitudinally spaced from one another. The first cuts overlap a portion of the second cuts. A step includes reapposing the dissection flap with the cut pattern against the wall of the body vessel where the dissection flap was detached from the wall such that the false lumen is closed off.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 3A-3I depict various cut patterns formed in a tissue flap.

DETAILED DESCRIPTION OF THE PREFERRED EMBODIMENTS

Methods for tissue treatment, and cutting devices or systems used for such treatment, and in particular, strategies to improve reapposition of a dissection flap and promote aortic remodeling are described herein to improve long-term outcomes of acute aortic dissections. In particular, it has been found that forming cuts into the dissection flap may increase the compliance of the flap and reduce flap stress during displacement to the outer wall. The flap tissue is at least partially cut in-situ or in vivo into the intima and deeper layers in order to reduce the tissue's resistance to displacement or to alleviate the circumferential strength of the intima. In some instances, one or more cuts, such as for example, openings or slits, are formed in the tissue in patterns by cutting systems or devices, which may be particularly beneficial in reapposing the dissection flap to the aortic wall with an expandable device to overcome difficulties due to contraction of the intima and/or expansion of the media and adventitia in the acute setting. The difficulty in reapposition of the flap may be due to the overall tension in the flap due to the aortic blood pressure and larger diameter blood vessels. The patterns may balance several factors: including stress distribution along the entire flap, reduction of peak stresses along the flap that weakens the flap and increases the risk of circumferential tearing, and the sufficient ratio of cut area to flap tissue area for remodeling and healing time. Cuttings systems may include any known cutting device for in-situ or in vivo procedures, including electrosurgical and mechanical blade devise, as described herein. In one example, a method includes the step of forming a cut in a dissection flap with a cutting device. A step includes inserting an expandable device within the true lumen. A step includes radially expanding the expandable device to reappose the dissection flap along a wall of the body vessel.

In the present application, the term "distal" when referring to a delivery device refers to a direction that is farthest away from the heart when an operator is using the delivery device, while the term "proximal" refers to a direction that is generally closest to the heart when the operator is using the delivery device. The distal and proximal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure.

Figure 1:
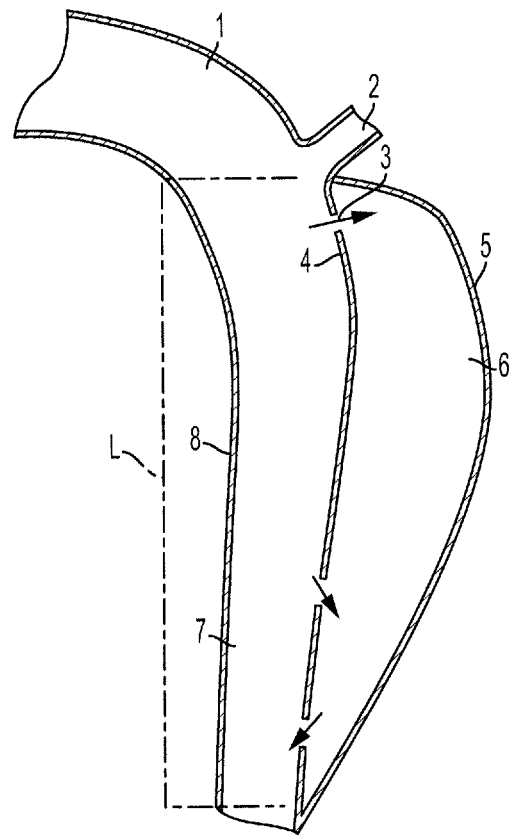
FIG. 1 is an illustration of a body vessel with a true lumen and false lumen, for example, an aortic dissection.
Figure 2:
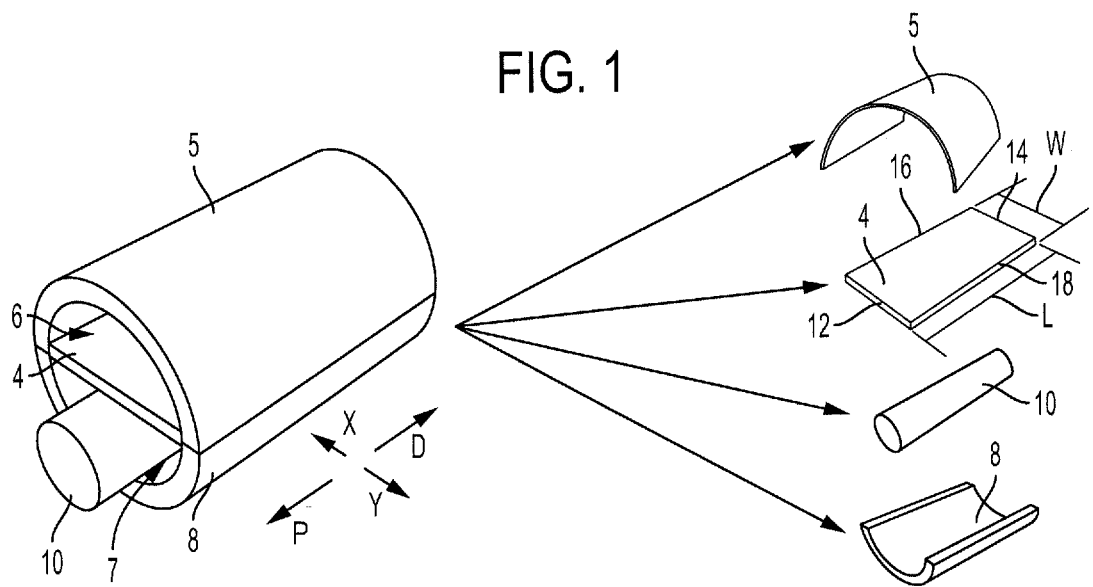
FIG. 2 depicts an expandable device inserted within a true lumen of a body vessel.

FIGS. 1-2 illustrate a non-limiting example of a type B dissection in a human aorta. A tear 3 in the inner layer of the vessel 1 distal to a subclavian artery 2 typically allows blood to enter into the aortic wall (see arrows) and longitudinally detach or peel an inner layer or flap 4 of the vessel 1 from an outer layer 5 or false lumen wall within a natural lumen of the aorta. The space created by the blood between the two layers is referred to as a false lumen 6. The tear 3 is referred as the primary entry point into the false lumen 6. The detached inner layer or flap 4 is disposed within the body vessel 1. The portion of the vessel 1 within the flap 4 of the vessel along the dissection is referred to as a true lumen 7. The vessel wall disposed along a length L of the flap 4 is indicated by true lumen wall 8. In some cases, multiple entry and exit openings may exist along the flap, as indicated by the flap openings. FIG. 2 depicts an expandable medical treatment device 10, such as but not limited to, a stent, a stent graft (shown), or a balloon, may be inserted in the true lumen 7 of the body vessel 1. The device 10 may be located in the true lumen of the body vessel 1 at the treatment site to be expanded to reappose the separated inner or flap 4 to the body vessel 1, as will be described.

The flap 4 may be shaped as a rectangle to include generally a width W and the length L. For example, the flap 4 may be characterized as having a first axial side 12 disposed at the tear 3 and associated with the proximal end and a second axial side 14, associated with the distal end, disposed longitudinally downstream from and distal to the first axial side 12 and where the body vessel wall layer remains intact and not separated. The longitudinal distance between the first axial side 12 and the second axial side 14 defines the length L of the flap 4. A first longitudinal direction, represented by arrow P, may be toward the first axial side 12, or also known as the proximal or upstream direction. A second longitudinal direction, represented by arrow D, may be toward the second axial side 14, or also known as the distal or downstream direction. The flap 4 may be defined as having a series of circumferential segments adjacent to one another between the first and second axial sides 12, 14. The flap 4 may be characterized as a having a first lateral side 16 and a second lateral side 18 extending between the first axial and second axial sides 12, 14. The lateral sides are defined at the locations where the body vessel wall layer remains intact and not separated. The lateral directions are generally perpendicular to the longitudinal directions. For instance, a first lateral direction, represented by arrow X, may be toward the first lateral side 16, or also known as the first circumferential direction, and a second lateral direction, represented by arrow Y, may be toward the second lateral side 18, or also known as the second circumferential direction, opposite the first circumferential directions. The chordal distance between the first lateral and second lateral sides 16, 18 defines the width W of the flap 4.

Up to complete reapposition of the flap 4 may be made easier by providing patterns of one or more cuts arranged within the flap. FIGS. 3A-3H depict examples of cut patterns. In an example of a first cut pattern 30 in FIG. 3A, a single cut 31 is formed in the flap 4. The cut 31 is shown disposed in an intermediate zone of the flap 4 between the first axial and second axial sides 12, 14 and the first lateral and second lateral sides 16, 18. The cut 31 is shown shaped as a linear slit having a small width relative to a longitudinal length. The longitudinal length of the cut 31 may be up to 40% of the length L of the flap 4. The cut length may be between about 1 to 5 cm, or, in one example, the cut length may be 3 cm.

Figure 3A:
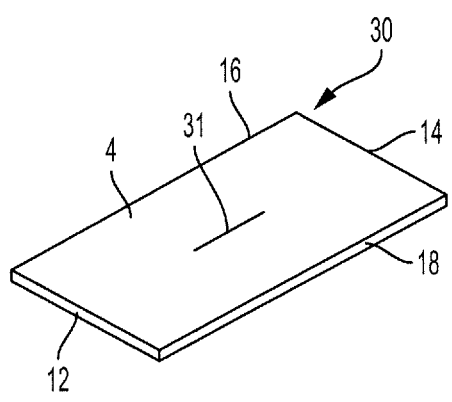
Figure 3B:
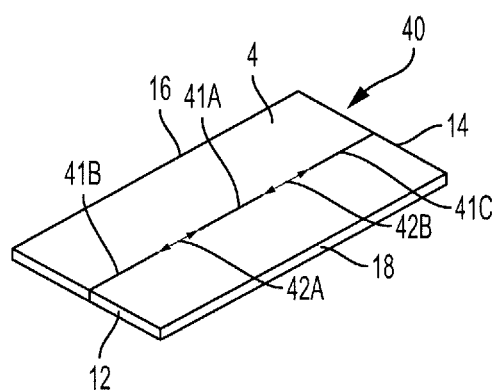

In an example of a second cut pattern 40 in FIG. 3B, a plurality of cuts 41A, 41B, 41C is formed in the flap 4. The first cut 41A is shown disposed in an intermediate zone of the flap 4 between the first axial and second axial sides 12, 14 and the first lateral and second lateral sides 16, 18. The second cut 41B is shown disposed extending distally from the first axial side 12 to a distal location longitudinally spaced by a bridge 42A from the first cut 41A. The third cut 41C is shown disposed extending proximally from the second axial side 14 to a proximal location longitudinally spaced by a bridge 42B from the first cut 41A. The second and third cuts 41B, 41C are shown in an intermediate zone of the flap 4 between the first lateral and second lateral sides 16, 18. The cuts 41A, 41B, 41C are shown shaped as a linear slit having a small width relative to a longitudinal length. The longitudinal length of the cuts 41A, 41B, 41C may be the same length or may be different lengths. The length of the cuts may be up to 40% of the length L of the flap 4. The second cut pattern 40 may be expanded with additional cuts. For example, additional intermediate cuts may be formed between the first cut 41A and the second and third cuts 41B, 41C, respectively, while maintaining the distances of the bridges, which may be constant or may vary. In one example, the cut length may be about 1 to 5 cm and the bridge length may be about 0.5 to 1.5 cm. In one example, the cut length may be about 3 cm and the bridge length may be about 0.5 cm. The second cut pattern showed a slight improvement (reduced by about 5 kPa) over the first cut pattern in the amount of average expansion stress required for full flap reapposition.

Figure 3C:
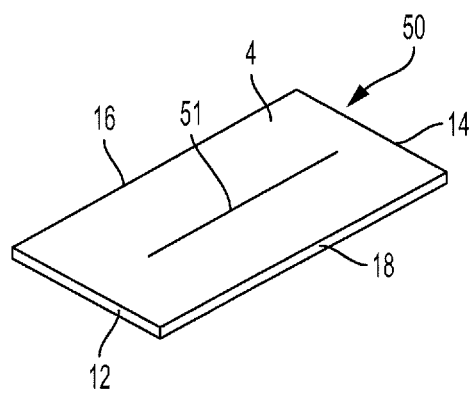

In an example of a third cut pattern 50 in FIG. 3C, a single cut 51 is formed in the flap 4. The cut 51 is shown disposed in an intermediate zone of the flap 4 between the first axial and second axial sides 12, 14 and the first lateral and second lateral sides 16, 18. The cut 51 is shown shaped as a linear slit having a small width relative to a longitudinal length. The longitudinal length of the cut 51 may be 40% to 70% of the length L of the flap 4. The cut length may be about 5 to about 8 cm. In another example, the cut length is about 6.5 cm. The third cut pattern showed a substantial improvement (reduced by over 50% or about 15 kPa) over the first cut pattern in the amount of average expansion stress required for full flap reapposition. The longer length of cut in the third cut pattern may also require additional healing time.

Figure 3D:
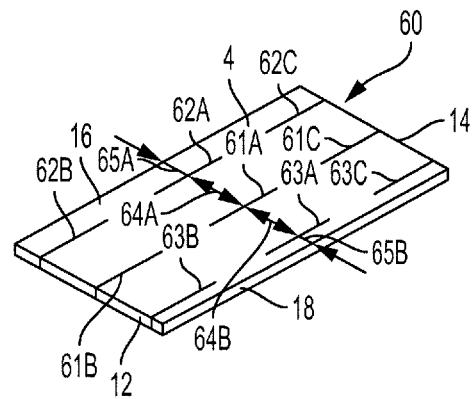

In an example of a fourth cut pattern 60 in FIG. 3D, a plurality of cuts 61A, 61B, 61C, 62A, 62B, 62C, 63A, 63B, 63C is formed in the flap 4. The cuts 61A, 61B, 61C are shown forming an intermediate first row. The cuts 62A, 62B, 62C form an outer second row laterally or circumferentially spaced from the intermediate first row by a first spacing 64A and laterally spaced from the first lateral side 16 by a first end spacing 65A. The first end spacing 65A may be smaller in distance than the first spacing 64A. The cuts 63A, 63B, 63C form an outer third row laterally or circumferentially spaced from the intermediate first row by a second spacing 64B and laterally spaced from the second lateral side 18 by a second end spacing 65B. The second end spacing 65B may be smaller in distance than the second spacing 64B. The first and second end spacings 65A, 65B may have the same distance between the respective cuts. Alternatively, the distances of first and second end spacings 65A, 65B may vary or be different. The first and second spacings 64A, 64B may have the same distance between each of the respective adjacent cuts or such distances may vary between the respective adjacent cuts.

In the intermediate first row, the first cut 61A is shown disposed in an intermediate zone of the flap 4 between the first axial and second axial sides 12, 14 and the first lateral and second lateral sides 16, 18. The second cut 61B is shown disposed extending distally from the first axial side 12 to a distal location longitudinally spaced by a bridge 66A from the first cut 61A. The third cut 61C is shown disposed extending proximally from the second axial side 14 to a proximal location longitudinally spaced by a bridge 66B from the first cut 61A. The second and third cuts 61B, 61C are shown in an intermediate zone of the flap 4 between the first lateral and second lateral sides 16, 18.

In the outer second row, the first cut 62A is shown disposed in an intermediate zone of the flap 4 between the first axial and second axial sides 12, 14. The second cut 62B is shown disposed extending distally from the first axial side 12 to a distal location longitudinally spaced by a bridge 67A from the first cut 62A. The third cut 62C is shown disposed extending proximally from the second axial side 14 to a proximal location longitudinally spaced by a bridge 67B from the first cut 62A.

In the outer third row, the first cut 63A is shown disposed in an intermediate zone of the flap 4 between the first axial and second axial sides 12, 14. The second cut 63B is shown disposed extending distally from the first axial side 12 to a distal location longitudinally spaced by a bridge 68A from the first cut 63A. The third cut 62C is shown disposed extending proximally from the second axial side 14 to a proximal location longitudinally spaced by a bridge 68B from the first cut 63A.

The cuts 61A, 61B, 61C, 62A, 62B, 62C, 63A, 63B, 63C are shown shaped as linear slits having a small width relative to a longitudinal length. The longitudinal length of the cuts 61A, 61B, 61C, 62A, 62B, 62C, 63A, 63B, 63C may be the same length or may be different lengths. The lengths of the cuts may be up to 40% of the length L of the flap 4. The bridges and cuts may be generally aligned longitudinally and laterally. The cut length may be about 1 to 5 cm and the bridge length is about 0.5 cm to 1.5 cm, and the circumferential spacing is about 1 to 3 cm. In one example, the cut length is about 3 cm and the bridge length is about 0.5 cm, and the circumferential spacing is about 2 cm. The fourth cut pattern showed a substantial improvement (reduced by over 50% or about 15 kPa) over the first cut pattern in the amount of average expansion stress required for full flap reapposition. In comparison with the third cut pattern, the fourth cut pattern showed a slight improvement in the amount of average expansion stress required for full flap reapposition. The peak stresses along the bridges may be higher than desirable.

The fourth cut pattern 60 may be expanded with additional cuts. For example, additional intermediate cuts may be formed between the first cuts 61A, 62A, 63A and the second and third cuts 61B, 61C, 62B, 62C, 63B, 63C, respectively, while maintaining the distances of the bridges and lateral spacings, whether constant or varying, between adjacent cuts and the lateral sides. For example, a fifth cut pattern 70 is shown in FIG. 3E, including a plurality of cuts 71A, 71B, 71C, 72A, 72B, 72C, 73A, 73B, 73C, 74A, 74B, 74C, 75A, 75B, 75C is formed in the flap 4. The fifth cut pattern 70 may be substantially the same as the fourth cut pattern 60, with the following clarifications. The cuts 71A, 71B, 71C, 72A, 72B, 72C, 73A, 73B, 73C may have the same general location and configuration as the cuts 61A, 61B, 61C, 62A, 62B, 62C, 63A, 63B, 63C, and for sake of time will not described in any more detail than what has already been described in relation to the fourth cut pattern 60. The cuts 74A, 74B, 74C, 75A, 75B, 75C form additional intermediate rows (the intermediate second row and the intermediate third row, respectively,) which are shown disposed within the first and second spacings 64A, 64B of the previous cut pattern, which are now referred to as spacings 78A, 78B, respectively.

In the intermediate second row, the first cut 74A is shown disposed in an intermediate zone of the flap 4 between the first lateral and second lateral sides 16, 18, and in particularly in the first spacing 78A between the cuts 72A, 71A. The second cut 74B is shown in the first spacing 78A disposed extending distally from the first axial side 12 to a distal location longitudinally spaced by a bridge 76A from the first cut 74A. The third cut 74C is shown in the first spacing 78A disposed extending proximally from the second axial side 14 to a proximal location longitudinally spaced by a bridge 76B from the first cut 74A.

In the intermediate third row, the first cut 75A is shown disposed in an intermediate zone of the flap 4 between the first lateral and second lateral sides 16, 18, and in particularly in the second spacing 78B between the cuts 73A, 71A.

The second cut 75B is shown in the second spacing 78B disposed extending distally from the first axial side 12 to a distal location longitudinally spaced by a bridge 77A from the first cut 75A. The third cut 74C is shown in the first spacing 64A disposed extending proximally from the second axial side 14 to a proximal location longitudinally spaced by a bridge 77B from the first cut 75A. The cut length may be about 1 to 5 cm and the bridge length is about 0.5 to 1.5 cm, and the circumferential spacing is about 0.5 to 1.5 cm. In one example, the cut length is about 3 cm and the bridge length is about 0.5 cm, and the circumferential spacing is about 1 cm. The fifth cut pattern showed a substantial improvement (reduced, by over 60%) over the first cut pattern in the amount of average expansion stress required for full flap reapposition. In comparison with the fourth cut pattern, the fifth cut pattern showed a slight improvement in the amount of average expansion stress required for full flap reapposition. The peak stresses along the bridges may be higher than desirable.

The next examples show the cuts in a longitudinally overlapping pattern. In an example of a sixth cut pattern 80 in FIG. 3F, a plurality of cuts 81A, 81B, 81C, 81D, 81E is formed in the flap 4. The cut 81A is shown disposed in an intermediate zone of the flap 4 between the first lateral and second lateral sides 16, 18. The cut 81B is laterally or circumferentially spaced from the cut 81A by a first spacing 84A and laterally or circumferentially spaced from the first lateral side 16 by a first end spacing 85A, and the cut 81C is laterally spaced from the cut 81A by a second spacing 84B and laterally spaced from the second lateral side 18 by a second end spacing 85B. The cuts 81A, 81B, 81C may be disposed extending from one of the first and second axial sides 12, 14 (for example, shown extending proximally from the second axial side 14).

The cuts 81D, 81E are formed at the opposite side of the cuts 81A, 81B, 81C (shown extending distally from the first axial side 12). The cut 81D is shown disposed within the first spacing 84A and laterally spaced from the cuts 81A, 81B and laterally spaced from the first lateral side 16 by a third end spacing 85C that is greater the first end spacing 85A. The cut 81E is shown disposed within the second spacing 84B and laterally spaced from the cuts 81A, 81C and laterally spaced from the second lateral side 18 by a fourth end spacing 85D that is greater the second end spacing 85B. The cuts 81A, 81B, 81C, 81D, 81E are shown shaped as linear slits having a small width relative to a longitudinal length. The longitudinal length of the cuts 81A, 81B, 81C, 81D, 81E may be the same length or may be different lengths. The lengths of the cuts may be more than 50% to less than the full length L of the flap 4. The ends of the cuts are shown longitudinally offset to form an overlapping pattern along an intermediate region. In one example, the degree of overlapping is such that the ends of the cuts are longitudinally positioned up anywhere between the end and up to the longitudinal center of the adjacent cut. The sixth cut pattern 80 may be expanded with additional cuts. For example, additional cuts may be formed along either side, while maintaining the distances of the bridges, which may be constant or may vary. The cut length may be about 4 to 8 cm and the bridge length may be about 0.5 to 1.5 cm, and the circumferential spacing may be about 1 to 3 cm between adjacent cuts and a length of 0.5 to 1.5 cm between cuts along intermediate region. In one example, the cut length is about 6 cm and the bridge length is about 0.5 cm, and the circumferential spacing is about 2 cm between adjacent cuts and the length of 1 cm between cuts along intermediate region. The sixth cut pattern showed a substantial improvement (reduced by over 80%) over the first cut pattern in the amount of average expansion stress required for full flap reapposition. In comparison with the fifth cut pattern, the sixth cut pattern showed a slight improvement in the amount of average expansion stress required for full flap reapposition. The peak stresses along the bridges may be higher than desirable. Although the sixth cut pattern showed the most improvement over the other disclosed cut patterns, the longer length of cuts in the sixth cut pattern may also require additional healing time.

The cuts in any of the cut patterns disclosed may have a variety of shapes and sizes. For example, the cuts may have an undulated, zigzag, or stepped shape or may have other shapes, regular or irregular. In an example of a seventh cut pattern 90 in FIG. 3G, a plurality of cuts 91A, 91B, 92A, 92B having an undulated, zigzag (shown), or stepped shape is formed in the flap 4. The cuts 91A, 91B are shown forming an intermediate first row. The cuts 92A, 92B form an intermediate second row laterally spaced from the intermediate first row by a first spacing 94 and laterally spaced from the first lateral side 16 by a first end spacing 95. The first end spacing 95 may have the same distance between the respective cuts. Alternatively, the distances of the first spacing 95 may vary or be different. The first spacing 94 may have the same distance between each of the respective adjacent cuts or such distances may vary between the respective adjacent cuts.

In the intermediate first row, the first cut 91A is shown disposed in an intermediate zone of the flap 4 between the first axial and second axial sides 12, 14 and the first lateral and second lateral sides 16, 18. The second cut 91B is shown disposed extending proximally from the second axial side 14 to a proximal location longitudinally spaced by a bridge 96A from the first cut 91A. In the intermediate second row, the first cut 92A is shown disposed extending distally from the first axial side 12 to a distal location longitudinally spaced by a bridge 96B from the second cut 92B. The second cut 92B is shown disposed extending proximally from the second axial side 14 to a proximal location longitudinally spaced by the bridge 96B from the first cut 92A.

The cuts 91A, 91B, 92A, 92B are shown shaped as slits having a small width relative to a longitudinal length. The longitudinal length of the cuts 91A, 91B, 92A, 92B may be the same length or may be different lengths. The lengths of the cuts may be up to 50% of the length L of the flap 4. The seventh cut pattern 90 may be expanded with additional cuts. For example, additional intermediate cuts may be formed between the cuts 91A, 92A and the cuts 91B, 92B, respectively, while maintaining the distances of the bridges and lateral spacings, whether constant or varying, between adjacent cuts and the lateral sides. The seventh cut pattern showed a substantial improvement (reduced by over 50%) over the first cut pattern in the amount of average expansion stress required for full flap reapposition.

In an example of an eighth cut pattern 100 in FIG. 3H, a plurality of cuts 101A, 101B, 101C, 102A, 102B, 103A, 103B is formed in the flap 4 in a longitudinally overlapping pattern. The cuts 101A, 101B, 101C are shown forming an intermediate first row. The cuts 102A, 102B form an outer second row laterally or circumferentially spaced from the intermediate first row by a first spacing 104A and laterally spaced from the first lateral side 16 by a first end spacing 105A. The first end spacing 105A may be smaller in distance than the first spacing 104A. The cuts 103A, 103B form an outer third row laterally or circumferentially spaced from the intermediate first row by a second spacing 104B and laterally spaced from the second lateral side 18 by a second end spacing 105B. The second end spacing 105B may be smaller in distance than the second spacing 104B. The first and second end spacings 105A, 105B may have the same distance between the respective cuts. Alternatively, the distances of first and second end spacings 105A, 105B may vary or be different. The first and second spacings 104A, 104B may have the same distance between each of the respective adjacent cuts or such distances may vary between the respective adjacent cuts.

In the intermediate first row, the first cut 101A is shown disposed in an intermediate zone of the flap 4 between the first axial and second axial sides 12, 14 and the first lateral and second lateral sides 16, 18. The second cut 101B is shown disposed extending distally from the first axial side 12 to a distal location longitudinally spaced by a bridge 106A from the first cut 101A. The third cut 101C is shown disposed extending proximally from the second axial side 14 to a proximal location longitudinally spaced by a bridge 106B from the first cut 101A. The second and third cuts 101B, 101C are shown in an intermediate zone of the flap 4 between the first lateral and second lateral sides 16, 18.

In the outer second row, the first and second cuts 102A, 102B are shown disposed in an intermediate zone of the flap 4 between the first axial and second lateral sides 16, 18. The first cut 102A is shown disposed distal to the first axial side 12 by a material spacer 108A. The second cut 102B is shown disposed proximal to the second axial side 14 by a material spacer 108B. The first cut 102A is shown longitudinally spaced by a bridge 107A from the second cut 102B. In the outer third row, the first and second cuts 103A, 103B are shown disposed in an intermediate zone of the flap 4 between the first axial and second lateral sides 16, 18. The first cut 103A is shown disposed distal to the first axial side 12 by a material spacer 109A. The second cut 103B is shown disposed proximal to the second axial side 14 by a material spacer 109B. The first cut 103A is shown longitudinally spaced by a bridge 107B from the second cut 103B.

The cuts 101A, 101B, 101C, 102A, 102B, 103A, 103B are shown shaped as slits having a small width relative to a longitudinal length. The longitudinal length of the cuts 101A, 101B, 101C, 102A, 102B, 103A, 103B may be the same length or may be different lengths. The lengths of the cuts may be up to 40% of the length L of the flap 4. The cut length may be about 1 to 5 cm, the bridge length is about 0.5 to 1.5 cm, the spacer length is about 1.5 to 2.5 cm, and the circumferential spacing is about 0.5 to 1.5 cm. In one example, the cut length is about 3 cm, the bridge length is about 0.5 cm, the spacer length is about 1.8 cm, and the circumferential spacing is about 1 cm. The eighth cut pattern showed a substantial improvement (reduced by over 40%) over the first cut pattern in the amount of average expansion stress required for full flap reapposition. In comparison with the other cut patterns, the eighth cut pattern showed the most improved results when also considering healing time and peak stress loads.

The size and number of cuts shown and described in any one of the disclosed patterns are for illustrative purposes, and may be varied accordingly. In one example, the eighth cut pattern 100 may be modified to include only two rows of cuts to form a ninth pattern 100A shown in FIG. 3I. For instance, the cuts 101A, 101B, 101C may form a first row not centrally located but further circumferentially offset, and the cuts 102A, 102B circumferentially spaced from the first row similar to the two row cut pattern in FIG. 3G.

Figure 4:
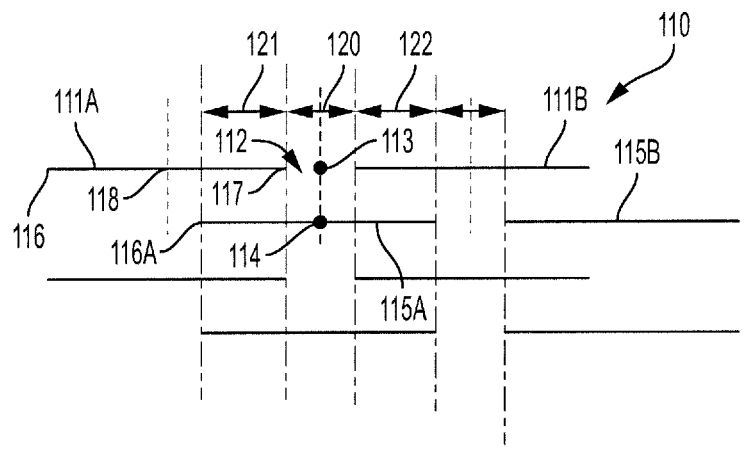
FIG. 4 illustrates a cut pattern with overlapping cuts.

FIG. 4 depicts an example pattern 110 of a longitudinally overlapping arrangement, where a cut overlaps a portion of an adjacent cut. The pattern 110 may include one or more of the cuts shown. The first cut 111A and the second cut 111B are longitudinally spaced from one another by the bridge 112. A longitudinal center 113 of the bridge 112 defined between longitudinally adjacent cuts 111A, 111B is disposed in alignment with a longitudinal center 114 of the cut 115A of cuts 115A, 115B that are laterally or circumferentially adjacent. Each of the cuts, for example cut 111A, includes a first end 116 associated with the proximal end and a second end 117 associated with the distal end. A longitudinal center 118 is defined at the midpoint (shown by the line) between the first end 116 and the second end 117. The first end 116A of the cut 115A is shown overlapping the second end 117 of the cut 111A, and the second end 117 of the cut 111A is shown overlapping the first end 116A of the cut 115A. The first end 116A of the cut 115A is positioned between the second end 117 of the cut 111A and the longitudinal center 118 of the cut 111A. The second end 117 of the cut 111A is positioned between the first end 116A of the cut 115A and the longitudinal center 114 of the cut 115A.

As shown in FIG. 4 and FIGS. 3F, 3G, 3H, and 3I, the overlapping pattern of the cuts may be arranged to provide each circumferential segment of the flap that is discontinuous, that is, a portion of at least one of the cuts is present within each circumferential segment along substantially the entire (for example, 50% to 100% of) flap length. FIG. 4 depicts three adjacent circumferential segments adjacent to one another along the flap, with the second circumferential segment 120 disposed between the first and third circumferential segments 121, 122. The second circumferential segment 120 may include portions of non-overlapping adjacent cuts, and the first and third segments 121, 122 may include portions of the overlapping adjacent cuts. The cut density of the circumferential segment of the flap is defined as the number of cuts per an area of circumferential segment of the flap. The second circumferential segment 120 may include a lower or smaller cut density than the cut density of at least one of the first and third segments 121, 122. In one example, the overlapping pattern of the cuts may be arranged to provide each circumferential segment of the flap that is discontinuous or interrupted by at least one cut, that is, a portion of at least one of the cuts is present within each circumferential segment along the entire flap length.

Figure 5:
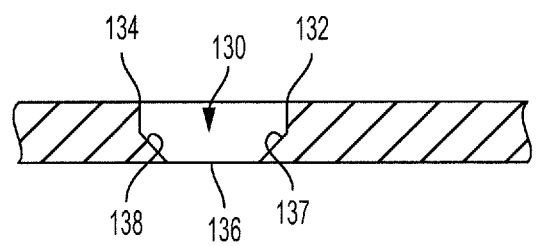
FIGS. 5-6 illustrate different cut configurations.
Figure 6:
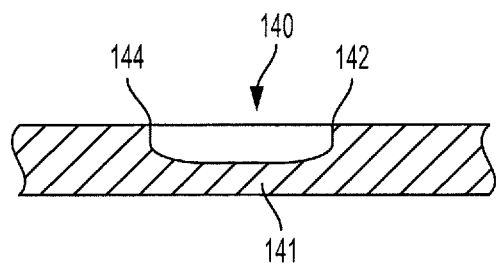

The term "cut" may be used herein to describe partial tissue cuts where a partial portion of tissue is cut into and/or partially removed and/or to describe full tissue cuts where tissue is cut into or removed fully to define a through opening in the body tissue. The cuts may be referred to as "slits" or "openings" and can have a variety of shapes, such as for example, rectangular, circular, elliptical, star-shaped. As described previously, the shape of the cuts may be linear or non-linear, such as having an undulated, zigzag, or stepped shape. In some instances, the shape of the cuts may be derivatives of the shapes disclosed or may be irregular due to the nature of the tissue, cutting device orientation, and other factors. Any one of the disclosed cuts may have a constant cross-sectional shape. FIG. 5 is a partial cross-sectional view of one example of any one of the disclosed cuts. The cut 130 includes a distal end 132 and a proximal end 134. An intermediate through opening 136 is bounded by a distal partial cut 137 extending from the distal end 132, and a proximal partial cut 138 extending from the proximal end 134 such that the cross-sectional shape of the cut varies. FIG. 6 is a partial cross-sectional view of another example of any one of the disclosed cuts. Here, a partial cut 140 is formed in a manner that there is not a through opening. A reduced wall 141 is formed between the distal end 142 and the proximal end 144. Any one of the patterns may include the same type of cuts or different cuts that vary along the body tissue.

The patterns disclosed herein may be formed by a variety of devices, and nonlimiting examples of cutting systems are described below. It is contemplated that other tissue cutting devices may be utilized for in-situ or in-vivo cutting operations. For example, an electrosurgical tissue cutting system using monopolar, bipolar, and/or sesquipolar RF energy generation, a laser system, an ultrasound or ultrasonic system, an electrical voltage resistive heating system, a mechanical blade system or scalpel, a microwave system, and a cryogenic fluid system.

Figure 7:
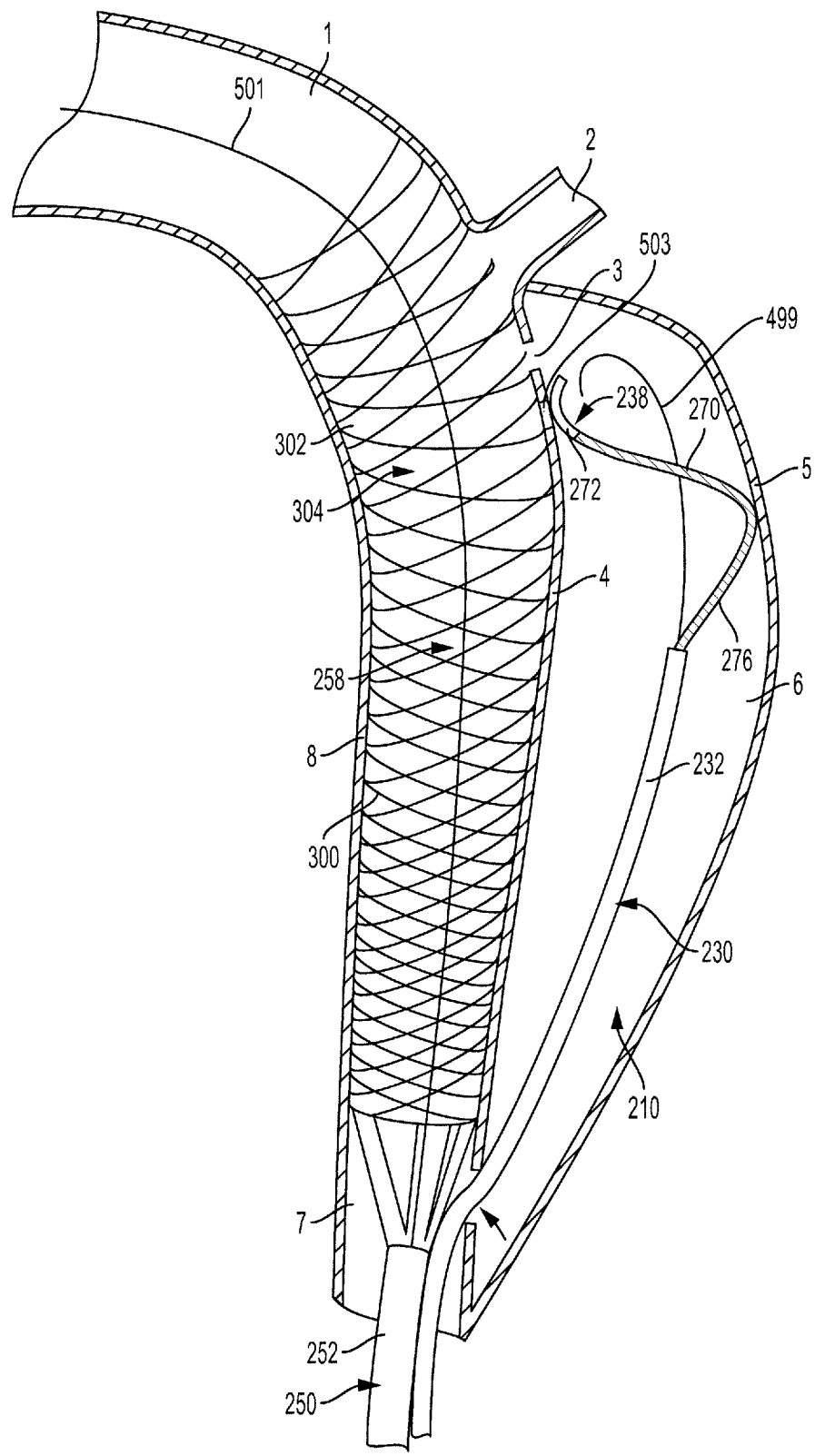
FIG. 7 depicts an example of an electrosurgical cutting system forming a cut in a tissue flap within a body vessel.

FIG. 7 depicts one example of a tissue cutting system that may be used for medical treatment. One such system 210 is more fully described in U.S. Provisional Application Ser. No. 62/459,344, entitled "Cutting System and Method for Tissue Cutting for Medical Treatment," filed on Feb. 16, 2017, which is hereby incorporated by reference in its entirety. Although the electrosurgical tissue cutting system 210 illustrates a sequipolar arrangement, suitable modifications to the system may convert the devices to a bipolar or monopolar arrangement, as understood by one of ordinary skill in the art.

The electrosurgical tissue cutting system 210 may include a power supply (not shown) in electrical communication with a first device 230 and a second device 250. For example, the first device 230 may be electrically connected via a conductor to one pole of a radio frequency (RF) generator RFG housed in the power supply. The second device 250 may be electrically connected to the other pole of the RF generator of the power supply. The first device 230 may include a first outer sheath 232 with a tubular body extending between a proximal end and a distal end and disposed about a first device longitudinal axis. The first outer sheath 232 is movable in the distal and proximal directions for selective deployment of a first cutting device 238 which may be housed within a longitudinal sheath lumen of the first outer sheath 232. The first outer sheath 232 may also include a side branch or other port for receiving the first electrical conductor.

The first cutting device 238 may have one or more conductive probes 270 having an energizable tip 272. The conductive probe 270 includes an elongated body of an electrical conductive material. An insulating jacket 276 may be disposed about the probe body, leaving the energizable tip 272 exposed. The probe body is shown having a curvilinear shaped portion proximate its proximal end, where the energizable tip 272 is located. As shown in FIG. 7, the energizable tip 272 includes an engagement region disposed at a curved bend (as shown), at an angular bend or corner, or planar region. The engagement region of the energizable tip 272 defines a tip surface area of electrical conductive material. The energizable tip 272 may also be disposed along a linear portion or other geometric shape portions to define a desired cut shape. When more than one conductive probe 270 is used, the extension length of each of the conductive probes may be about the same length or longitudinally offset to create one of the disclosed cut patterns. Connector members (not shown) may be coupled in between adjacent conductive probes 270 to fix the circumferential spacing between the conductive probes 270 when separated in the deployed configuration.

The second device 250 may comprise a second outer sheath 252 with a tubular body extending between a proximal end and a distal end disposed about a second device longitudinal axis. The second outer sheath 252 is movable in the distal and proximal directions for selective deployment of a second cutting device 258, which may be housed within a longitudinal sheath lumen of the second outer sheath 252. The second outer sheath 252 may also include a side branch in communication with the sheath lumen of the second outer sheath 252 for allowing the passage of the second electrical conductor. The second electrical conductor extends farther within the sheath lumen for electrical connection to the second cutting device 258.

The second cutting device 258 is shown having an expandable body 300 that includes an outer surface 302 with an electrical conductive material 304. The expandable body 300 is movable between a radially contracted configuration and a radially expanded configuration. The amount of the electrical conductive material 304 defines an outer surface area when the second cutting device 258 is in its radially expanded configuration. The outer surface area of is at least greater than the tip surface area of the energizable tip. In one example, the ratio between the outer surface area of the expandable body 300 to the tip surface area defines a sesquipolar electrode arrangement.

In one example, the expandable body 300 may be defined by a metal frame comprised of at least a proximal tapered section and a body or barrel section distal to the proximal tapered section. The metal frame of the body section may comprise of a wire mesh or woven structure, strut framework, or other stent frame structure, such as a cannula cut stent, that can be radially compressible and expandable. The body section is shown extending axially at a uniform cross-sectional profile or cylindrical profile, although the body section may have an outward or inward curvature or may taper along the axis in the proximal direction to have an increasingly larger or smaller cross-sectional area profile along different regions of the body section for better conformity within the body vessel. In another example, the expandable body 300 may include an inflatable balloon device. Here, an inner cannula of the balloon device is surrounded by a balloon membrane sealably attached to the inner cannula at proximal and distal attachment locations. The inner cannula is configured to receive inflation fluid. Continued inflation at a suitable pressure causes the balloon membrane to radially expand. In the radially expanded configuration, the balloon membrane may be shaped to have a proximal tapered section, a working body section, and a distal tapered section. The inflation fluid may be an electrically non-conductive to inhibit electrical energy flow into the first device outside the conductive surface. The working body section may define a cylindrical shape as shown or may be tapered for better conformity with the body vessel. Removal of the inflation fluid from the inflation annular lumen at the distal end of the second device via the inflation lumen causes the balloon membrane to deflate and radially compress into a smaller profile. The second outer sheath may be included for selectively sliding over the balloon membrane when in the deflated configuration.

The first device 230 and the second device 250 of the electrosurgical tissue cutting system 210 work in coordination for cutting tissue based on the electrical power or current delivered by the power supply to a contacted, or target, portion of tissue within a patient. The tissue primarily contemplated is an aorta dissection flap; however, other applications of the system 210 may include small blood vessels in need of cauterization, tumor, or other undesirable tissue to be removed from the patient. The first device 230 and the second device 250 may be configured to be manipulated by a human operator and/or a robot.

For example, the RF generator RFG of the power supply may include a RF energy generator such that electrical current flows to the energizable tip 272 of the first cutting device 238 of the first device 230 (or active electrode), and the expandable body 300 of the second cutting device 258 of the second device 250 (or return electrode), which are cooperatively operative to form the cut. The energizable tip 272 and the expandable body 300 are disposed across from each other on the obverse sides of the tissue to be cut or perforated in engagement with the tissue sides. The RF energy generator may be suitable for sesquipolar or other configurations. Electric current may be oscillated between the energizable tip 272 and the expandable body 300. When the first cutting device 238 includes more than one conductive probe 270, the energizable tips 272 may be sequentially energized during power. For example, the energizable tips 272 may remain deployed and axially move along the tissue, while the tips 272 are sequentially phased on and off. In this arrangement, the cuts formed in the tissue are formed one at a time. The selective energization may be controlled by the control switch or there may be a switching module (hardware or software) included with the power supply. In another example, the energizable tips may be energized at the same time during oscillation to form more than one cut at a time. When energized, the smaller tip surface area of the energizable tip 272 and the larger cross-sectional area of the expandable body 300 are operable together to form a cut into the tissue by tissue vaporization and RF arc generation, as appreciated by those of skill in the art. The RF arc at the tissue is generated, with the energizable tip 272 as the active electrode and the expandable body as the return probe, which directs energy at the tissue interface. The RF arc is most intense at the engagement region of the energizable tip 272, which may move toward the expandable body with pressure. The cutting current may be constant, intermittent or a combination of both. In one example, the cutting current is constant for cutting without coagulation.

The electrical conductive material described above for any of the components may include platinum, gold, copper and/or silver, or alloys thereof. In one example, the conductive probe may be made of a shape memory alloy such as Nitinol. Other conductive materials may be used without departing from the scope of this disclosure. Portions of the first device and/or the second device may be covered in electrical insulation or may be otherwise insulated such that the first and second cutting devices may deliver electrical energy from the power supply to the contacted tissue. The electrical insulation may be any appropriate electrically insulating material including, but not limited to, plastic, rubber, vinyl, epoxy, parylene, or ceramic and may enable the operator to grasp the devices as well as protect the patient's body.

Figure 8:
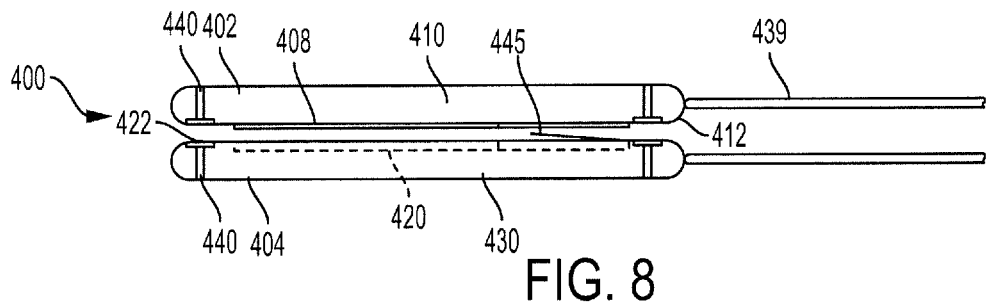
FIGS. 8-9 depict another example of a mechanical blade cutting system and its cutting operation.
Figure 9:
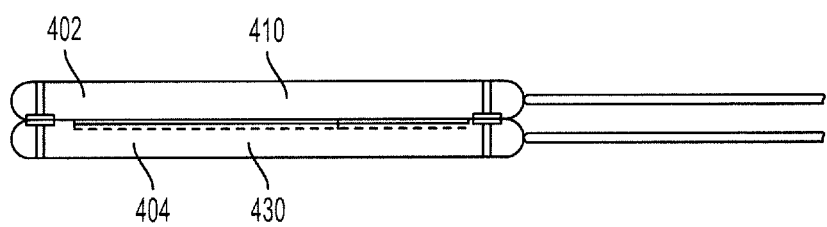
Figure 10:
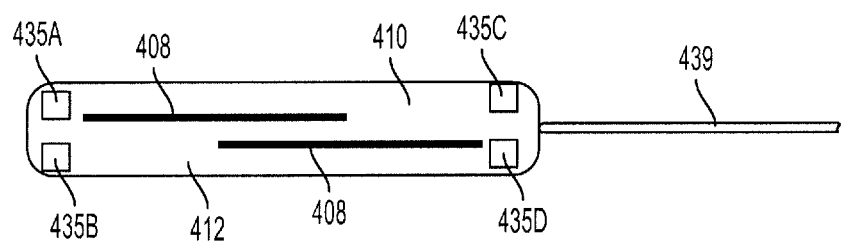
FIG. 10 depicts one example of a first cutting device of the system in FIGS. 8-9.

FIGS. 8-9 illustrate another example of a tissue cutting system 400. The tissue cutting system 400 includes a pair of cutting devices 402, 404 cooperatively operable to form a cut into a tissue wall or flap. With additional reference to FIG. 10, the first device 402 includes at least one blade 408 (two shown) coupled to a device body 410. In one example, the first device 402 includes a single blade in either of the positions shown or other positions such as centrally located. Features may be included to the first device to guard or shield the blade from inadvertent engagement with unintended tissues. The blade or blades 408 may be oriented, arranged, and sized to define partially or fully one of the disclosed cut patterns listed above. The blade(s) may selectively or permanently protrude away from a confronting surface 412 of the device body that faces the second device and the tissue during operation. In this example, two blades are shown longitudinally offset similar to a portion of the eighth cut pattern. The blade may comprise a metal, such as stainless steel, having a sharpened edge suitable for cutting body tissue, such as the dissection flap or intima layer of the wall.

Figure 11:
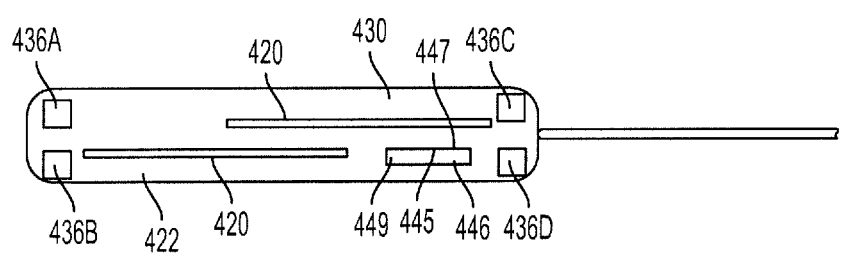
FIG. 11 depicts one example of a second cutting device of the system in FIGS. 8-9.

With additional reference to FIG. 11, the second device 404 includes at least one blade recess 420 (two shown) formed in a confronting surface 422 of a device body 430. The blade recess or recesses 420 may be complementarily arranged in a mirror image pattern of the blades 408 of the first device 402. In the instance of a single blade device, a single recess may be present and arranged accordingly. The blade recesses(s) are sized and shaped to receive the blades 408. The tissue cutting system 400 includes a non-cutting configuration (shown in FIG. 8) where the devices do not sliceably engage the tissue and allow for relative movement between the devices, and a cutting configuration (shown in FIG. 9) where the devices form cuts in the tissue by the devices movement against one another. In one example, each body may include a blade and a cooperatively placed recess.

The bodies 410, 430 made of biocompatible materials, as understood in the art, may house one or more magnetic devices, that is, magnets or electromagnets, used for aligning the blades and blade recesses in the longitudinal and circumferential directions during the cutting operation. For example, the body 410 includes four magnetic devices 435A, 435B, 435C, 435D having a complementary polarity for coupling with the four magnetic devices 436A, 436B, 436C, 436D of the body 430. In other words, pairs of magnetic devices (435A, 436B), (435B, 436A), (435C, 436D), and (435D, 435C) have a complementary polarity for coupling. Adjacent magnetic devices, such as devices 435A, 435B, may have opposite polarity such that magnetic devices 436A, 436B are only attracted to the correct magnetic device. In one example, the magnetic devices 435A, 435B, 435C, 435D, 436A, 436B, 436C, 436D of at least one of the bodies are selectively magnetic to control the coupling and cutting operation. The magnetic devices are coupled to electrical energy via internal wiring or circuits that is coupled to a power conductor, which is shown extending through a cannula 439) to a power supply external to the patient. The selective energization may be controlled by a control switch or there may be switching module (hardware or software) included with the power supply.

The magnets may be rare earth magnets or electromagnets having sufficient magnetic power and strength to attract and align another source of magnetic attraction such as the magnets of the other device in-vivo. The magnets may include the neodymium-iron-boron compositions and cobalt-samarium compositions. Any number of individual magnets (e.g., zero, one, two, three, four, five, six, seven, or eight or more, etc.) may be provided. These magnets may located inside, outside, or combination thereof of the body of the devices, and may be positioned anywhere along the length of the bodies. Each magnet may be fixed in or on the bodies by any suitable method, for example, embedded in, adhered to or friction fit within the bodies. The magnets may have alternating polarity (for example, each magnet may have the opposite polarity as any adjacent magnets), the same polarity, or combinations thereof. The electromagnets may be activated, for example, selectively activated or may be activated one at a time to help ensure a certain alignment orientation with respect to the magnets to the other devices, for example, the more proximal magnets may be activated prior to activating the more distal magnets. In another example, the magnets may be activated in sequence, or alternatively, two or more magnets may be activated simultaneously to promote secure attachment to the other magnets.

The bodies 410, 430 may have imagable indicators 440 coupled or otherwise formed with the bodies, which are visible under fluoroscopic guidance or some other method of imaging. The imagable indicators 440 configured in a manner that permits identification of particular areas that correspond to a feature of particular importance on the device. The imagable indicator 440 may include an ultrasonically reflective surface, such as providing a series of indentations in the surface of the device that are configured to reflect sound waves and allow for ultrasound imaging of that particular region. As with the radiographically imagable structure, the ultrasonically reflective surface would be located at selected points along the device that correspond with a particular critical feature or structure thereof. In another example, the imagable indicators 440 may include radiopaque markers at selected locations that would indicate if the devices become tilted at or following deployment.

One or both of the devices 402, 404 may include a repel mechanism 445 to aid in separating the devices after a forming a cut. For example, the repel mechanism 445 may take the form of a leaf spring 446 having an end 447 attached to the confronting surface 422 of one of the bodies, such as the body 430, and an opposite end 449 spaced and biased from the confronting surface 422. The repel mechanism 445 may be provided both of the bodies. The magnetic force generated by the device magnets is greater than the repelling force of the repel mechanism 445, which allows the devices 402, 404 to couple and form the cuts. For example, when the magnets are electromagnets that are deactivated, the repel mechanism 445 is operable to push against the corresponding opposite body to move the devices away from each other.

The blades 408 may be retractable. The blades 408 may be spring biased in a manner such that when activated the blades protrude out, and when deactivated the blades 408 retract within the body. The bodies 410, 430 may include a shield or a shroud (not shown) around the blade 408. For example, the shroud may form a boundary around the blade. The shroud may be spring biased in a manner such that when activated the shroud may protrude out, and when deactivated the shroud retracts within the body. The device bodies 410, 430 may be configured for tracking along a guidewire. For example, the bodies may include a longitudinal bore for allowing the body to track along the guidewire. The longitudinal bore may be in fluid communication to the lumen within the cannula 439. In one example, the cutting system includes a first and second cutting devices. At least one of the cutting devices includes at least one blade, and the other cutting device includes a blade recess configured to receive the blade. Each of the first and second cutting devices may include magnetic devices for selective coupling to one another for completing a cutting operation. At least one of the first and second cutting devices may include a repel mechanism operable to move the devices away from each other. The first and second cutting devices may be cooperatively operative to form the cut. The cutting devices may include an cannula extending to a cutting device body and may include a guidewire lumen extending through the body and cannula.

FIGS. 8-9 depict aspects of the operation of the device. One of the devices 402, 404 may be inserted and positioned along one side of the body tissue, such as into the true lumen, and the other of the devices may be inserted along the opposite side of the body tissue, such as into the false lumen, similar to the system in FIG. 7, such that the body tissue or flap is disposed between the devices 402, 404. The devices 402, 404 may be positioned along the desired site of treatment. The magnets of one of the devices are magnetically attracted to the magnets of the other device to move from the non-cutting configuration to the cutting configuration. The shape of the blade and blade recess and the insertion of the blade into the blade recess are cooperatively operative to form a cut or cuts. For example, if the magnets are electromagnets, the electromagnets may be electrically activated in a manner known in the art for the cutting operation and deactivated to allow the devices to be moved and repositioned for another cutting operation.

Figure 12:
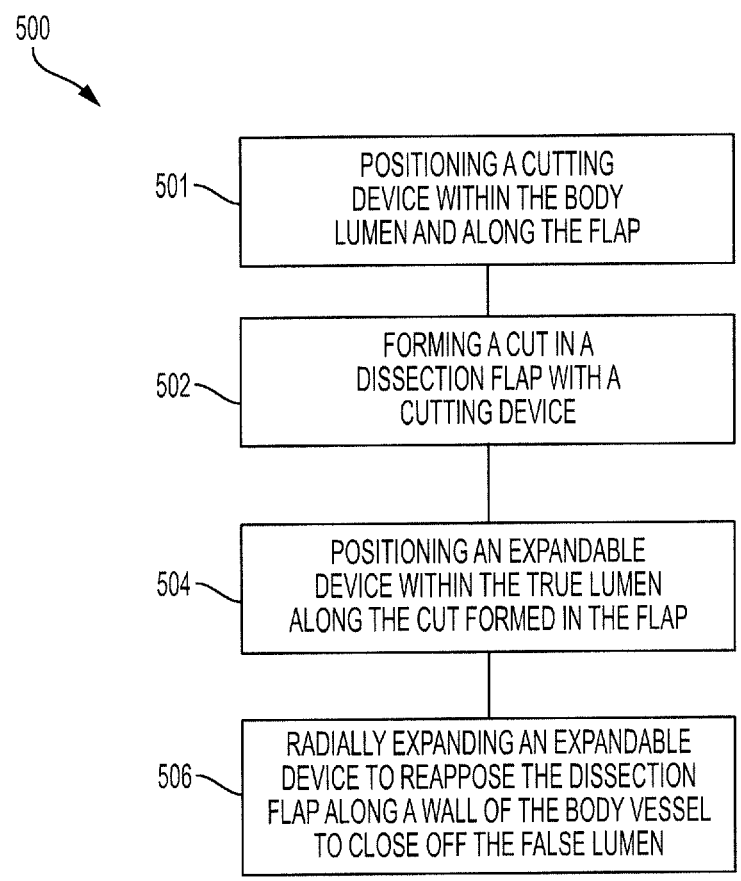
FIG. 12 is a flow diagram of an example of a method of treatment.

Methods of cutting a tissue, such as, for example, an aortic dissection flap, will now be described. A flow diagram describing an example method 500 is provided in FIG. 12. As may be appreciated by one of ordinary skill in the art, other methods of cutting a tissue, such as but not limited to, methods of treating blood vessels in need of cauterization or fistulas, or methods of removing tumors or other undesirable tissue. The order of the steps described below may be altered or adjusted, and some of the steps may be omitted or combined with other steps. As described above, at step 501, the one or more cutting devices or systems may be inserted and positioned within at least one of a true lumen and a false lumen and moved to a position along a dissection flap where treatment is desired.

In step 502, a cut is formed in a body tissue with any one of the disclosed cutting devices or systems. In one example body tissue, a cut may be formed in a dissection flap. For example, the cut may be formed in-situ or in-vivo into the intima flap in order to reduce the tissue's resistance to displacement or to alleviate the circumferential strength of the intima flap. Prior to formation of the cut or cuts, any one of the disclosed cutting devices or systems is inserted within the body vessel. The cutting system may include a single cutting device or more than one cutting devices that are cooperatively operative to form the cut. Guidewires may be introduced from a femoral artery or other known artery method into an aorta or the body vessel. For example, with reference to FIG. 7, a first guidewire 499 may be located along the first side of the body tissue, for example, from the main or true lumen of aorta and into the false lumen 6, and a second guidewire 501 may be placed along the opposite side of the body tissue, for example, into the true lumen 7. The first guidewire may be extended through a flap opening that provides access into the false lumen. Any one of the disclosed cutting devices may be inserted over the second guidewire for tracking along the first body tissue side, for example, into the true lumen, and the other of the cutting devices may be inserted over the first guidewire and tracked to a position along the second body tissue side, for example, into the false lumen. The cutting devices are located against the obverse sides of the tissue, such as the dissection flap. The cutting devices are appropriately positioned along the treatment site. For example, the cutting device may be positioned initially along the proximal end such that the devices may be retracted distally to form additional cuts along the body tissue.

After the cutting devices are correctly positioned along the body tissue, any one of the disclosed cutting devices may be activated to form a cut or cuts (shown as cut 503 in FIG. 7), as appreciated by one of skill in the art. Activation of the cutting devices may take various forms, as previously described, depending on the kind of the cutting device(s) used, for example, an electrosurgical tissue cutting system using monopolar, bipolar, and/or sesquipolar RF energy generation, a laser system, an ultrasound or ultrasonic system, an electrical voltage resistive heating system, a mechanical blade system or scalpel, a microwave system, and a cryogenic fluid system. For example, when the cutting devices are electrosurgical, activation may take the form of providing selective electrical power or current from the power supply to (thereby energizing) the first and second cutting devices, as described previously. In another example, electromagnets may be activated in a manner known in the art for the cutting devices with a blade to press down against each other and form the cuts.

As described previously, one or more of cuts 503 may be formed at step 502, which may comprise a single operation forming a single cut or plurality of cuts or subsequent operation to forming additional single or plurality of cuts with any one of the disclosed cutting devices. For example, the cutting devices may be configured to perform multiple cuts during a single cutting action. In other examples, the cutting devices may be moved relative to one another along the respective body tissue sides, for example, within the respective true lumen and false lumen. Subsequent activations of the cutting devices may be performed to form the additional cuts, for example, in one of the cut patterns disclosed herein. More than one cut pattern disclosed herein may be formed together to form a new pattern. For example, a second cut may be formed in the dissection flap with the cutting devices and longitudinally disposed from the first cut. A third cut may be formed in the dissection flap with the cutting devices, and circumferentially disposed from the first cut and the second cut. The third cut may be circumferentially disposed from and overlapping the first cut and the second cut. In another example, the second cut in the dissection flap formed with the cutting devices is circumferentially disposed from the first cut, and the third cut is longitudinally disposed from the first or second cuts.

Figure 13:
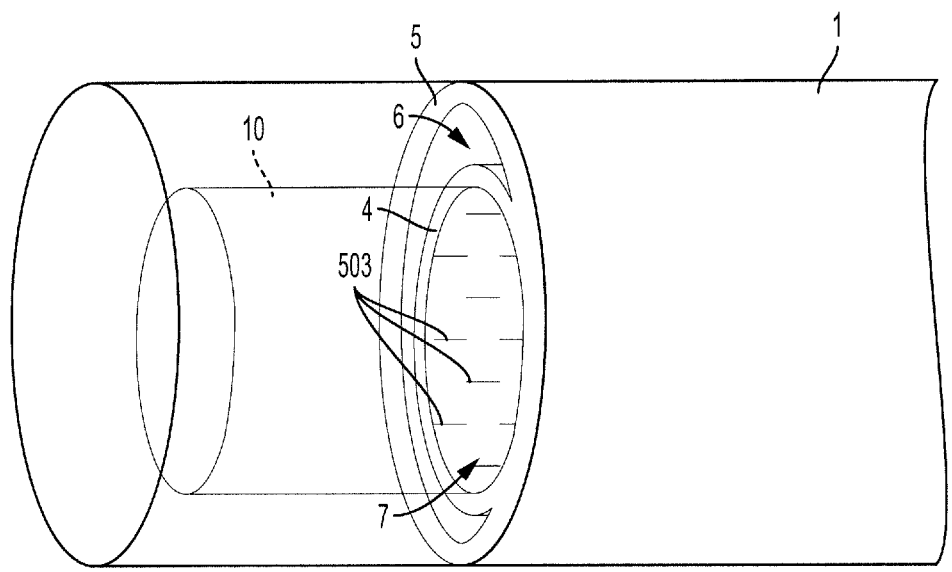
FIGS. 13-14 depict expansion of a true lumen with a subsequent expandable device after usage of the tissue cutting system.
Figure 14:
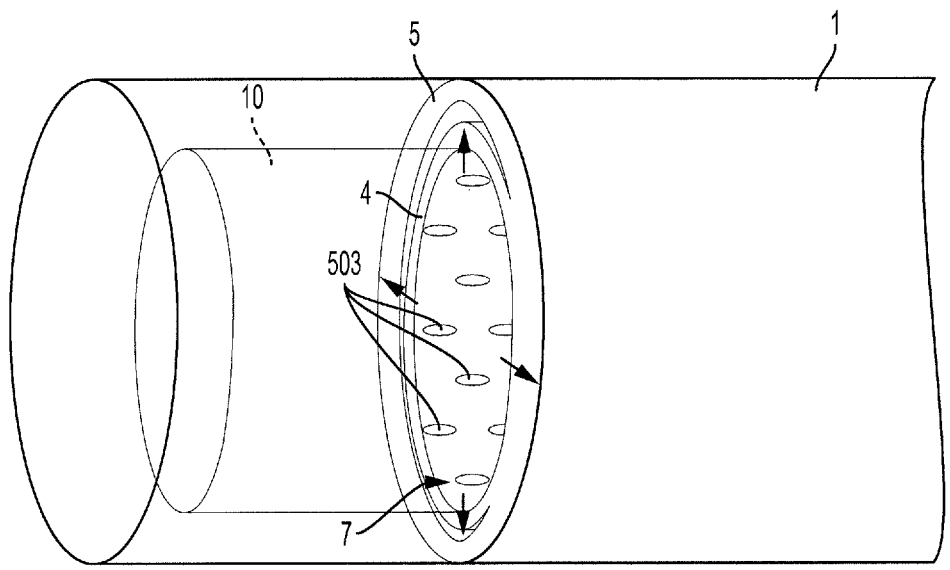

It has been found that the formation of the cuts into the tissue, such as dissection flap, may reduce the expansion stress or pressure required to fully reappose the flap with the outer wall of the body vessel. The cuts and cut patterns in the tissue may change the deformation mechanism of the flap from strain of the flap into bending of the tissue between the cuts. As a result of the deformation mechanism change, the reapposition of a cut or fenestrated flap may be less dependent on the aortic pressure or body vessel size. To this end, similar patterns may be used in any size body vessel. The expansion pressure may be provided by the expandable device 10 inserted within the body vessel 1 and permitted to radially expand, as shown in FIG. 2 and FIGS. 13-14. The expandable device 10 may be sized accordingly to provide suitable expansion pressure in addition to the aortic pressure that is transmitted to the flap. In some cut patterns, the average stress and peak stress during full reapposition have been found to be improved by the cut or fenestrated flap. In one example, better stress distribution along the longitudinal length has been found in cut patterns with some degree of overlapping cuts along the entire flap length. In other words, each circumferential segment of the flap is to some degree discontinuous or interrupted by at least one cut. Circumferential segments without any cuts may provide regions of the flap, such as the bridges, with increased peak stresses that may cause unintended circumferential tearing during full reapposition step. Healing capability and/or time of the dissection flap may also be a factor with higher density of cuts or longer cut lengths impacting this factor.

In step 504, the expandable device 10 is inserted and positioned into the body vessel 1 along the first body tissue side of the flap 4 where the cuts are formed, such as within the true lumen 7, as shown in FIG. 13. After a suitable number of cuts are formed into the separated inner layer or flap and the cutting system is removed from the body, other medical treatment devices, such as but not limited to, expandable stents, expandable stent grafts, or inflatable balloons, can be inserted in the true lumen of the body vessel. These radially expandable devices may be located in the true lumen of the body vessel along the cut zone as the treatment site. In step 506, the expandable device 10 is radially expanded to reappose the dissection flap 4 against a wall 5 of the body vessel 1 to close the false lumen 6. FIG. 14 shows the process to full re-apposition. The cross-sectional area of the cuts 503 may become more fully open or expand when the flap is reapposed. This reapposition step may allow thrombosing of the false lumen and promote aortic remodeling to improve long-term outcomes of acute aortic dissections and maintaining patency of the true lumen to re-establish the original flow lumen of the body vessel, such as the aorta, and to facilitate healing of the vessel. The fenestrated flap may also allow for more blood to be squeezed out of the false lumen, thereby avoid the pooling of blood within the false lumen.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A method of treatment for a body vessel, the body vessel having a dissection flap formed from a wall of the body vessel, the dissection flap longitudinally separating a natural body vessel lumen into a true lumen and a false lumen, the method comprising:
    positioning a cutting device within at least one of the true lumen and the false lumen and along the dissection flap;
    forming a cut pattern comprising a plurality of cuts in the dissection flap with the cutting device;
    positioning an expandable device within the true lumen along one of the plurality of cuts formed in the dissection flap; and
    radially expanding the expandable device to reappose the dissection flap with the cut pattern comprising the plurality of cuts against the wall of the body vessel where the dissection flap was detached from the wall such that the false lumen is closed off.

2. The method of claim 1, wherein the plurality of cuts comprises at least a first cut and a second cut in the dissection flap, wherein the second cut is longitudinally disposed from the first cut, circumferentially disposed from the first cut, or both longitudinally and circumferentially disposed from the first cut.

3. The method of claim 2, further comprising forming a third cut in the dissection flap with the cutting device, wherein the third cut is circumferentially disposed from the first cut and the second cut.

4. The method of claim 2, further comprising forming a third cut in the dissection flap with the cutting device, wherein the third cut is circumferentially disposed from and overlapping portions of the first cut and the second cut.

5. The method of claim 1, wherein the plurality of cuts includes a first cut and a second cut, wherein the second cut is circumferentially disposed from the first cut.

6. The method of claim 1, wherein each of the plurality of cuts is longitudinally and circumferentially offset from at least one other of the plurality of cuts.

7. The method of claim 1, wherein the cutting device is a first cutting device, the positioning step further comprising positioning the first cutting device within the false lumen and along the dissection flap, and the method further comprising positioning a second cutting device within the true lumen and along the dissection flap prior to the forming step, wherein the first and second cutting devices are cooperatively operative to form the plurality of cuts.

8. The method of claim 7, wherein the first and second cutting devices are electrically operable devices.

9. The method of claim 7, wherein at least one of the first and second cutting devices includes a blade, each of the first and second cutting devices including magnets for selective coupling, and at least one of the first and second cutting devices including a repel mechanism operable to move the devices away from each other.

10. The method of claim 1, wherein the expandable device is an expandable stent or stent graft.

11. The method of claim 1, wherein the expandable device is an inflatable balloon.

12. A method of treatment for a body vessel, the body vessel having a dissection flap formed from a wall of the body vessel, the dissection flap longitudinally separating a natural body vessel lumen into a true lumen and a false lumen, the method comprising:
forming a cut pattern in a dissection flap with a cutting system, the cut pattern comprising a first cut and a second cut circumferentially spaced and longitudinally offset from another;
positioning an expandable device within the true lumen and along the cut pattern formed in the dissection flap; and
expanding the expandable device to reappose the dissection flap with the cut pattern against the wall of the body vessel where the dissection flap was detached from the wall such that the false lumen is closed.

13. The method of claim 12, wherein the cut pattern comprises a first row of first cuts longitudinally spaced from one another, and a second row of second cuts longitudinally spaced from one another, wherein a bridge is defined between adjacent first cuts, wherein a longitudinal center of the bridge is in alignment with a longitudinal center of one of the second cuts.

14. The method of claim 13, wherein one of the first cuts is disposed at least at one of a distal end and a proximal end of the dissection flap.

15. The method of claim 13, wherein the first row of cuts and the second row of cuts are arranged to define discontinuous circumferential segments along the dissection flap.

16. The method of claim 15, wherein the discontinuous circumferential segments comprise a first circumferential segment and a second circumferential segment, where the second circumferential segment includes a cut density that is less than a cut density of the first circumferential segment.

17. The method of claim 12, wherein an end of the second cut is disposed along the first cut at a location between an end of the first cut and a longitudinal center of the first cut.

18. The method of claim 12, wherein at least one of the first cut and the second cut comprises a linear shape or an undulated or zigzag shape.

19. A method of treatment for a body vessel, the body vessel having a dissection flap formed from a wall of the body vessel, the dissection flap longitudinally separating a natural body vessel lumen into a true lumen and a false lumen, the method comprising:
forming a cut pattern in the dissection flap, the cut pattern comprising a first row of first cuts and a second row of second cuts circumferentially spaced from the first row, wherein the first cuts are longitudinally spaced from another one and the second cuts are longitudinally spaced from one another, wherein the first cuts overlap a portion of the second cuts;
and
reapposing the dissection flap with the cut pattern against the wall of the body vessel where the dissection flap was detached from the wall such that the false lumen is closed off.

20. The method of claim 19, further comprising inserting a first cutting device within the false lumen along the dissection flap and inserting a second cutting device within the true lumen along the dissection flap opposite to the first cutting device prior to the forming step, wherein the first and second cutting devices are cooperatively operative to form the cut pattern.

* * * * *